United States Patent
Robichaud et al.

(10) Patent No.: US 10,265,212 B2
(45) Date of Patent: Apr. 23, 2019

(54) SET OF OCCLUSAL SPLINTS AND METHOD OF MAKING SAME

(71) Applicant: PANTHERA DENTAL INC., Quebec (CA)

(72) Inventors: Diane Robichaud, Quebec (CA); Jacques Houde, Quebec (CA)

(73) Assignee: PANTHERA DENTAL INC., Quebec, Quebec (CA)

( * ) Notice: Subject to any disclaimer, the term of this patent is extended or adjusted under 35 U.S.C. 154(b) by 411 days.

(21) Appl. No.: 14/490,168

(22) Filed: Sep. 18, 2014

(65) Prior Publication Data

US 2015/0075542 A1 Mar. 19, 2015

Related U.S. Application Data

(60) Provisional application No. 61/879,436, filed on Sep. 18, 2013.

(51) Int. Cl.
*A61F 5/56* (2006.01)

(52) U.S. Cl.
CPC ........ *A61F 5/566* (2013.01); *A61F 2005/563* (2013.01)

(58) Field of Classification Search
CPC ... A61F 5/566; A61F 5/56; A61C 5/14; A63B 71/085; A63B 2071/088; A63B 2071/086; A61B 1/24
See application file for complete search history.

(56) References Cited

U.S. PATENT DOCUMENTS

| | | | |
|---|---|---|---|
| 5,592,951 A * | 1/1997 | Castagnaro | A61F 5/566 128/848 |
| 6,053,168 A * | 4/2000 | Sue | A61F 5/566 128/859 |
| 6,645,250 B2 | 11/2003 | Schulter | |
| 6,652,275 B2 * | 11/2003 | Byers | A45D 44/22 433/140 |
| 7,698,014 B2 | 4/2010 | Dunne et al. | |
| 7,770,582 B2 | 8/2010 | Chen | |
| 7,936,911 B2 | 5/2011 | Fang et al. | |

(Continued)

FOREIGN PATENT DOCUMENTS

| CA | 2713122 A1 | 7/2009 |
|---|---|---|
| CN | 102551892 A | 7/2012 |

(Continued)

OTHER PUBLICATIONS

Guinn, "Frequently Asked Questions", Utah Jaw Pain Clinic, http://www.utahjawpain.com/faq-s.php, downloaded 2014.

(Continued)

*Primary Examiner* — Ophelia A Hawthorne
(74) *Attorney, Agent, or Firm* — Merchant & Gould P.C.

(57) ABSTRACT

A set of occlusal splints includes a maxillary splint engageable over a maxillary superior dental arch of a mouth; and a mandibular splint engageable over a mandibular dental arch of the mouth. Each one of the maxillary splint and the mandibular splint is substantially U-shaped with an anterior section and two posterior sections extending from opposite ends of the anterior section. Each one of the maxillary splint and the mandibular splint has an inner wall surface defining a cavity shaped and configured to encase teeth of the corresponding one of the dental arches and an opposed outer wall surface, the outer wall surface having a contact surface at the anterior section. The maxillary and mandibular splints are operable in a contact configuration, wherein the contact surfaces of the maxillary and mandibular splints are abutted one against the other, and wherein an occlusal face of the posterior sections are spaced apart from one another.

24 Claims, 5 Drawing Sheets

(56) References Cited

U.S. PATENT DOCUMENTS

| | | | |
|---|---|---|---|
| 8,074,659 B2 | 12/2011 | Hanna | |
| 8,359,114 B2 | 1/2013 | Steingart et al. | |
| 8,485,197 B2* | 7/2013 | Metz | A61C 7/08 |
| | | | 128/848 |
| 2006/0003292 A1 | 1/2006 | Lauren et al. | |
| 2013/0239978 A1* | 9/2013 | Stubbs | A61C 7/006 |
| | | | 128/861 |

FOREIGN PATENT DOCUMENTS

| | | |
|---|---|---|
| RU | 2009107784 A1 | 9/2010 |
| WO | 2010087824 A1 | 8/2010 |
| WO | 2012034191 A1 | 3/2012 |

OTHER PUBLICATIONS

Crack-A-Smile Dental, "Night Guards", 2003, http://www.angelfire.com/ut2/crackasmile0/night.html.

Padmanabhan et al, "Inter-disciplinary management of a patient with severely attrited teeth" Indian Society Periodontology, 2010, http://www.ncbi.nlm.nih.gov/pmc/articles/PMC3100864/.

Resmed. "Narval CC", http://www.resmed.com/int/products/narval_cc/commercialinarval-cc.html?nc=dealers, 2012.

Dunn et al., "CAD/CAM Occlusal splints: A new paradigm", Austrasalian Dental Practice, 2011, clinical I Excellence, pp. 130-134.

Singh, "The forgotten implant: subperiosteal", Implant Tribune, vol. 4, No. 11, 2009, pp. 1-8.

* cited by examiner

SET OF OCCLUSAL SPLINTS AND METHOD OF MAKING SAME

CROSS-RELATED REFERENCE TO RELATED APPLICATION

This application claims priority under 35 USC § 119(e) of U.S. Provisional Patent application No. 61/879,436, which was filed on Sep. 18, 2013, the specification of which is hereby incorporated by reference.

FIELD OF THE INVENTION

The present invention relates to the field of protective devices for the mouth. More particularly, the present invention relates to a set of occlusal splints.

BACKGROUND

An occlusal splint is a dental appliance adapted to fit upper (maxillary) or lower (mandibular) arches of teeth, for protecting the teeth against mandibular dysfunction, such as bruxism, by aiding in preventing grinding of the teeth and excessive clenching.

There is a need for an improved system which, by virtue of its design and components, would further protect the temporomandibular joint. The temporomandibular joint is a hinge articulation between the upper and lower jaws. More particularly, the joint comprises a bone from the lower jaw (the mandible) which moveably fits inside a capsule formed within the upper temporal bone which is part of the cranium (skull). The clenching action of the posterior teeth of the upper jaw against those of the lower jaw, tends to act as a lever which may dislocate the mandibular bone from the capsule of the upper temporal bone.

SUMMARY

The object of the present invention is to provide a device which, by virtue of its design and components, satisfies at least some of the above-mentioned needs and is thus an improvement over other related occlusal splint systems known in the prior art.

In accordance with the present invention, the above mentioned object is achieved, as will be easily understood, by a set of occlusal splints such as the one briefly described herein and such as the one exemplified in the accompanying drawings.

According to a general aspect, there is provided a set of occlusal splints comprising: a maxillary splint adapted to fit a maxillary dental arch of a mouth; and a mandibular splint adapted to fit a mandibular dental arch of the mouth, each one of the maxillary splint and the mandibular splint having an anterior section and two posterior sections extending from opposite ends of the anterior section, and each one of the maxillary splint and the mandibular splint having a body with an inner portion shaped and configured to encase teeth of the corresponding dental arch and an opposed outer portion, the outer portion having a planar contact surface at the anterior section and occlusal faces at the posterior sections, and the maxillary and mandibular splints being operable in a contact configuration, wherein the planar contact surfaces of the maxillary and mandibular splints are abutted one against the other along a contact plane, the posterior sections of at least one of the maxillary splint and the mandibular splint being recessed in relation to the contact plane, in order to space apart matching occlusal faces of the posterior sections of the maxillary and mandibular splints from one another when the maxillary and mandibular splints are joined in the contact configuration.

In an embodiment, at least the mandibular splint comprises recessed posterior sections with respect to the contact plane.

In an embodiment, the body of each one of the maxillary splint and the mandibular splint comprises an inner wall surface substantially conforming to the shape of the teeth of the corresponding dental arch.

In an embodiment, the anterior section of each one of the maxillary splint and the mandibular splint covers anterior teeth and at least the first premolar of the corresponding arch when engaged therewith. In an embodiment, the anterior teeth consist of the incisors and the canines.

In an embodiment, the bodies of the maxillary splint and the mandibular splint comprise an outer wall surface and, in the posterior sections, the outer wall surface reproducing a shape of the teeth covered by the corresponding one of the maxillary splint and the mandibular splint.

In an embodiment, the planar contact surfaces of the maxillary splint and the mandibular splint extend substantially parallel to one another.

In an embodiment, the maxillary splint and the mandibular splint are free of mechanical connector extending therebetween when worn.

In an embodiment, the maxillary splint and the mandibular splint are disconnected from one another when worn.

In an embodiment, the occlusal faces of the posterior sections of the maxillary and mandibular splints are spaced apart from one another by at least 0.8 mm.

According to another general aspect, there is provided a set of occlusal splints, comprising: a maxillary splint engageable over a maxillary dental arch of a mouth; and a mandibular splint engageable over a mandibular dental arch of the mouth, each one of the maxillary splint and the mandibular splint having an anterior section and two posterior sections extending from opposite ends of the anterior section, and each one of the maxillary splint and the mandibular splint having an inner portion shaped and configured to encase teeth of the corresponding one of the dental arches and an opposed outer portion, the outer portion having a contact surface at the anterior section, and the maxillary splint and the mandibular splint being operable in a contact configuration, wherein the contact surfaces of the maxillary and mandibular splints are abutted one against the other, and wherein corresponding ones of the posterior sections are spaced apart, in order to protect the articulation between upper and lower jaws of the mouth.

In an embodiment, the contact surfaces are substantially planar.

In an embodiment, the outer portion comprises occlusal faces in the posterior sections and at least the mandibular splint comprises recessed occlusal faces in the posterior sections with respect to a contact plane defined between the contact surfaces in the contact configuration. The occlusal faces of the posterior sections of the maxillary and mandibular splints can be spaced apart from one another by at least 0.8 mm.

In an embodiment, each one of the maxillary splint and the mandibular splint comprises an inner wall surface substantially conforming to the shape of the teeth of the corresponding dental arch.

In an embodiment, the anterior section of each one of the maxillary splint and the mandibular splint covers anterior teeth and at least the first premolar of the corresponding arch when engaged therewith. In an embodiment, the anterior teeth consist of the incisors and the canines.

In an embodiment, the maxillary splint and the mandibular splint comprise an outer wall surface and, in the posterior sections, the outer wall surface reproducing a shape of the teeth covered by the corresponding one of the maxillary splint and the mandibular splint.

In an embodiment, the contact surfaces of the maxillary splint and the mandibular splint extend substantially parallel to one another.

In an embodiment, the maxillary splint and the mandibular splint are free of mechanical connector extending therebetween when worn.

In an embodiment, the maxillary splint and the mandibular splint are disconnected from one another when worn.

According to still another aspect, there is provided a set of occlusal splints, comprising: a maxillary splint engageable over a maxillary superior dental arch of a mouth; and a mandibular splint engageable over a mandibular dental arch of the mouth, each one of the maxillary splint and the mandibular splint being substantially U-shaped with an anterior section and two posterior sections extending from opposite ends of the anterior section, and each one of the maxillary splint and the mandibular splint having an inner wall surface defining a cavity shaped and configured to encase teeth of the corresponding one of the dental arches and an opposed outer wall surface, the outer wall surface having a contact surface at the anterior section, and the maxillary and mandibular splints being operable in a contact configuration, wherein the contact surfaces of the maxillary and mandibular splints are abutted one against the other, and wherein an occlusal face of the posterior sections are spaced apart from one another.

In an embodiment, the contact surfaces are substantially flat.

In an embodiment, at least the mandibular splint comprises recessed occlusal faces in the posterior sections with respect to a contact plane defined between the contact surfaces in the contact configuration.

In an embodiment, each one of the maxillary splint and the mandibular splint comprises an inner wall surface substantially conforming to the shape of the teeth of the corresponding dental arch.

In an embodiment, the anterior section of each one of the maxillary splint and the mandibular splint covers anterior teeth and at least the first premolar of the corresponding arch when engaged therewith. In an embodiment, the anterior teeth consist of the incisors and the canines.

In an embodiment, in the posterior sections, the outer wall surface of the maxillary splint and the mandibular splint reproduces a shape of the teeth covered by the corresponding one of the maxillary splint and the mandibular splint.

In an embodiment, the contact surfaces of the maxillary splint and the mandibular splint extend substantially parallel to one another.

In an embodiment, the maxillary splint and the mandibular splint are free of mechanical connector extending therebetween when worn.

In an embodiment, the maxillary splint and the mandibular splint are disconnected from one another when worn.

According to a further aspect, there is provided a set method of making a set of occlusal splints for a mouth. The method comprises: obtaining a model of a maxillary dental arch of the mouth; obtaining a model of a mandibular dental arch of the mouth; configuring the models of the maxillary and mandibular dental arches in a contact configuration; and conceiving a maxillary splint and a mandibular splint using the models of the maxillary and mandibular dental arches in the contact configuration, each one of the splints having an anterior section and two posterior sections extending from opposite ends of the anterior section, an inner wall surface defining a cavity shaped and configured to encase teeth of the respective one of the maxillary dental arch and the mandibular dental arch and an opposed outer wall surface having a contact surface at the anterior section, wherein in the contact configuration, the contact surfaces of the maxillary and mandibular splints are contacted and the posterior sections are spaced apart from one another.

Other objects, advantages and features of the present invention will become more apparent upon reading of the following non-restrictive description of embodiments thereof, given for the purpose of exemplification only, with reference to the accompanying drawings.

BRIEF DESCRIPTION OF THE DRAWINGS

It will be noted that throughout the appended drawings, like features are identified by like reference numerals.

DETAILED DESCRIPTION

Figure 1:
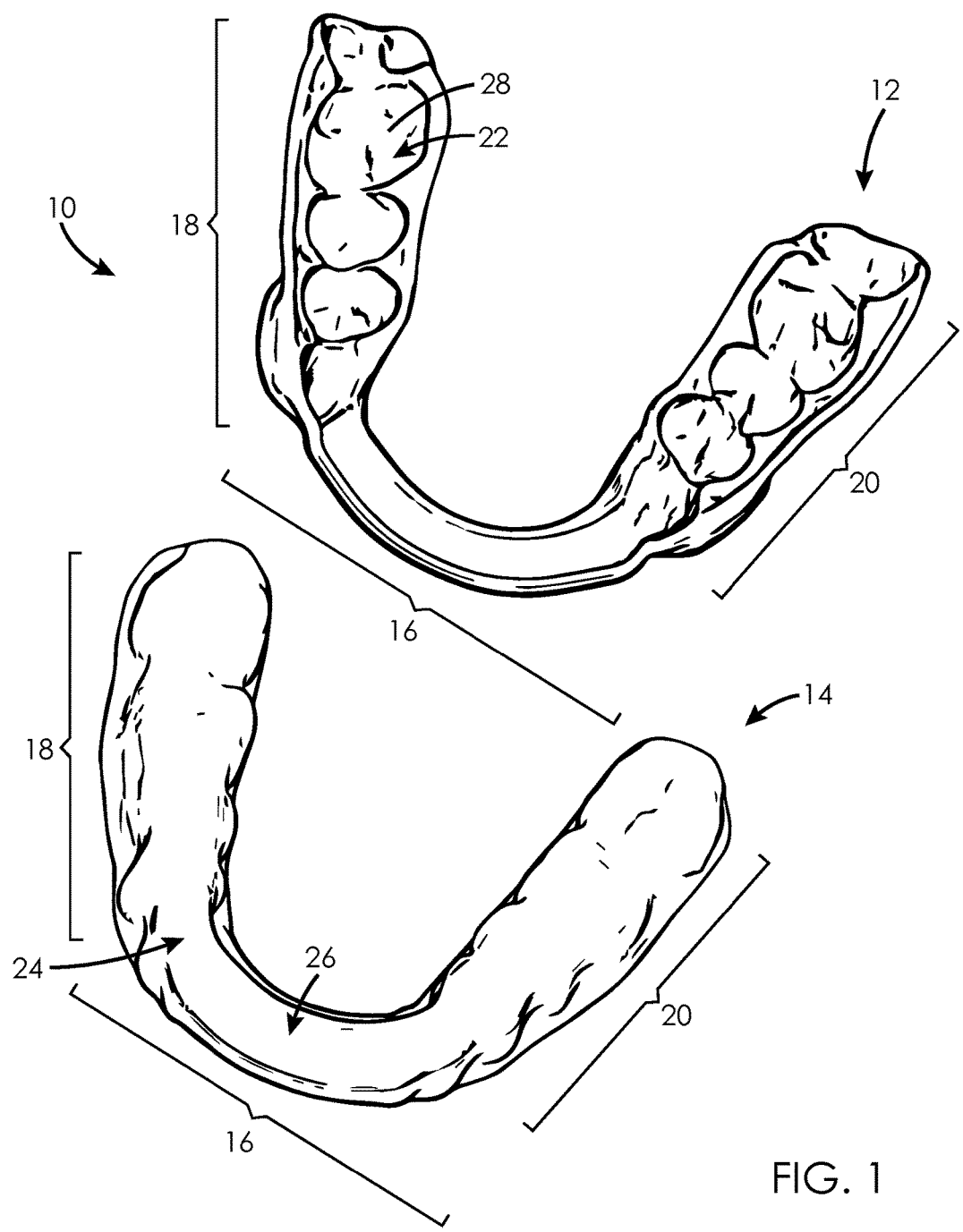
FIG. 1 is a top perspective view of a set of occlusal splints, in accordance with an embodiment, the set including a maxillary splint and a mandibular splint, spaced-apart from one another.
Figure 2:
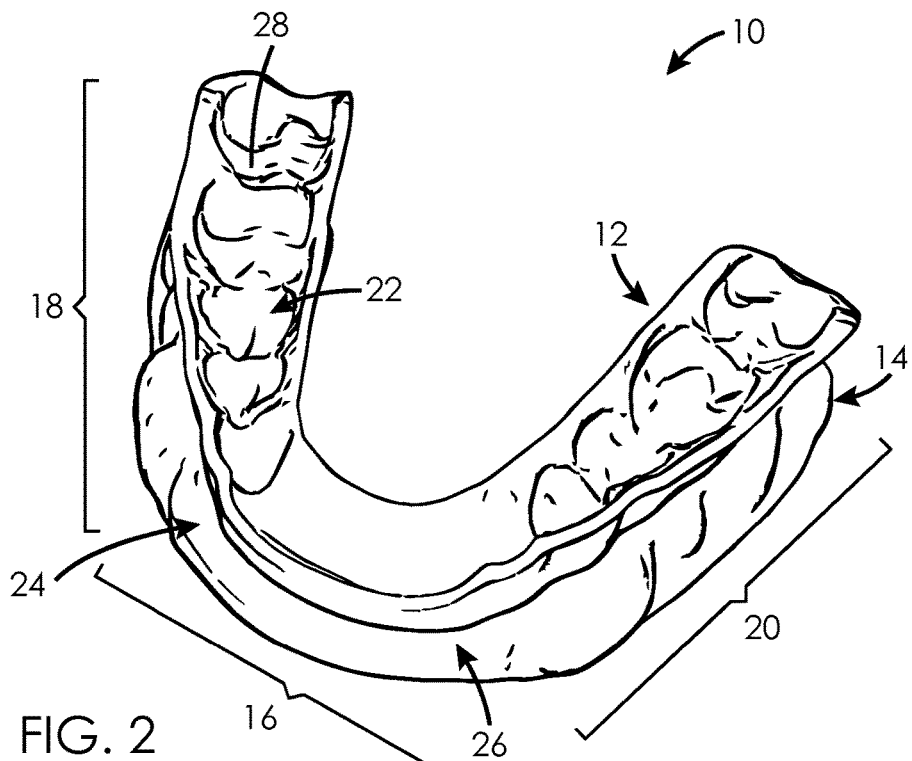
FIG. 2 is a top perspective view of the set of occlusal splints of FIG. 1, the set of occlusal splints being shown in a contact configuration.
Figure 3:
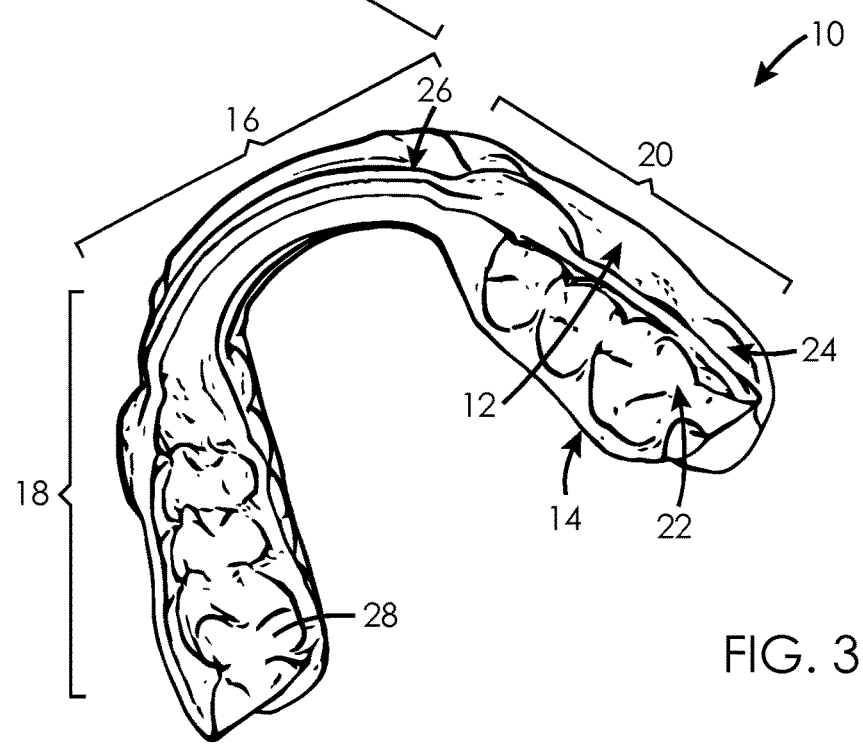
FIG. 3 is a bottom perspective view of the set of occlusal splints in the contact configuration shown in FIG. 2.

In the following description, the same numerical references refer to similar elements. The embodiments, geometrical configurations, materials mentioned and/or dimensions shown in the figures or described in the present description are embodiments only, given for exemplification purposes only.

Although the embodiments as illustrated in the accompanying drawings comprises particular components and although the embodiment of the set of occlusal splints and corresponding parts thereof consist of certain geometrical configurations as explained and illustrated herein, not all of these components and geometries are essential and thus should not be taken in their restrictive sense, i.e. should not be taken as to limit the scope of the present invention. It is to be understood, as also apparent to a person skilled in the art, that other suitable components, and cooperation therebetween, as well as other suitable geometrical configurations and materials may be used for the set of occlusal splints, as will be briefly explained herein and as can be easily inferred herefrom, by a person skilled in the art, without departing from the scope of the invention.

Broadly described, a set of occlusal splints, in accordance with an embodiment, as exemplified in the accompanying drawings, sets apart at least the posterior teeth of the upper and lower jaws, i.e. the maxillary and mandibular jaws, in order to prevent the posterior teeth to produce a lever effect when they are clenched or contacted together, so as to avoid dislocating the mandibular bone from the capsule of the upper temporal bone. It is appreciated that occlusal splints can also be referred to as night guards and occlusal plates.

According to an embodiment, and as better illustrated in FIGS. 1 to 9, there is provided a set of occlusal splints 10, comprising a maxillary splint 12 adapted to fit a maxillary (or superior or upper) dental arch of a mouth, and a mandibular splint 14 adapted to fit a mandibular (or inferior or lower) dental arch of the mouth. More particularly, the maxillary splint 12 is engageable over the maxillary dental arch (not shown) and the mandibular splint 14 is engageable over the mandibular dental arch (not shown). From a top and a bottom plan view, each splint 12, 14 is substantially U-shaped and has an anterior section 16 and two posterior sections 18, 20 extending from opposite ends of the anterior section 16. As shown in FIGS. 1 to 9, the anterior section 16 is defined substantially by a front area of each splint 12, 14 which is intended to receive the anterior teeth, including the incisors and the canines, and the first premolars of the corresponding dental arch. Optionally, in some implementations and depending on the size of the mouth, the anterior section 16 can also receive the second premolars. More particularly, the anterior section 16 engages and covers the anterior teeth, the first premolars, and, optionally, the second premolars of the corresponding dental arch. The posterior sections 18, 20 are intended to receive the posterior teeth of the corresponding dental arch, i.e. the molars, and, optionally, with the second premolars. More particularly, the posterior sections 18, 20 engage and cover posterior teeth and, optionally, the second premolars of the corresponding dental arch. Other configurations of the anterior section 16 and the posterior sections 18, 20 are also possible, as will be better explained further below.

Each splint 12, 14 comprises a body 25 with an inner portion 22 including an inner wall surface 28 defining a teeth receiving cavity 30. The inner portion 22, including its teeth receiving cavity 30, is shaped and configured to encase teeth of the corresponding dental arch. The body of each splint 12, 14 also has outer portion 24, opposed to the inner portion 22, and including an outer wall surface 32. The outer portion 24 of each splint 12, 14 comprises a contact surface 26 at the anterior section 16, which will be described in more details below. The outer portion 24 of each splint 12, 14 also comprises occlusal faces 34 in the posterior sections 18, 20. The occlusal faces 34 of the splints 12, 14 correspond to the chewing surface of the posterior teeth.

Figure 4:
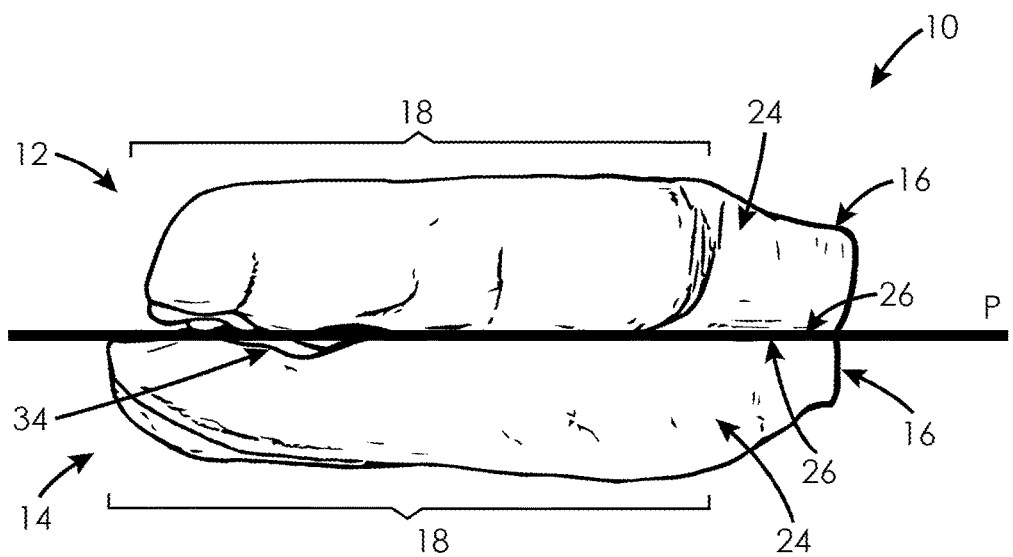
FIG. 4 is a side elevation view of the set of occlusal splints in the contact configuration shown in FIG. 2.
Figure 5:
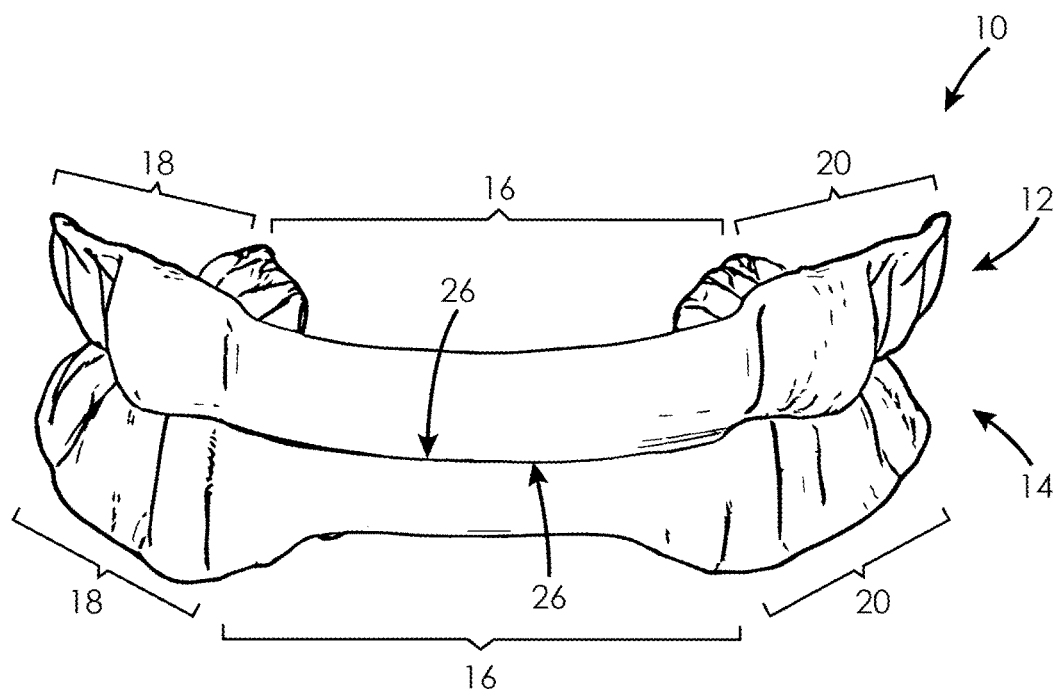
FIG. 5 is a front elevation view of the set of occlusal splints in the contact configuration shown in FIG. 2.
Figure 6:
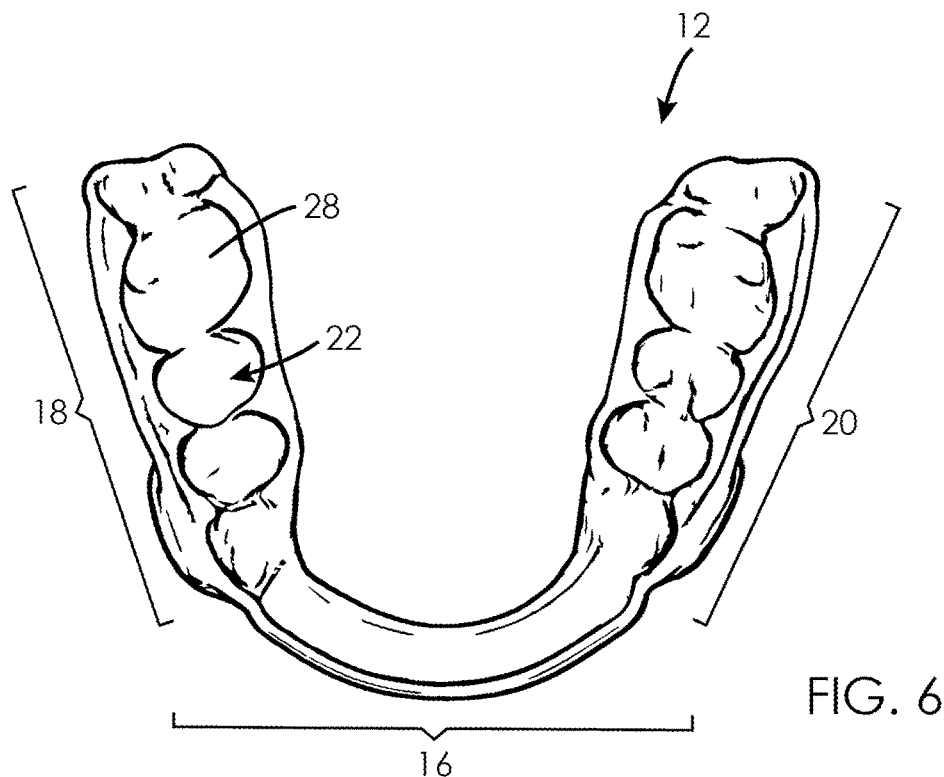
FIG. 6 is a top plan view of the maxillary splint shown in FIG. 1.
Figure 7:
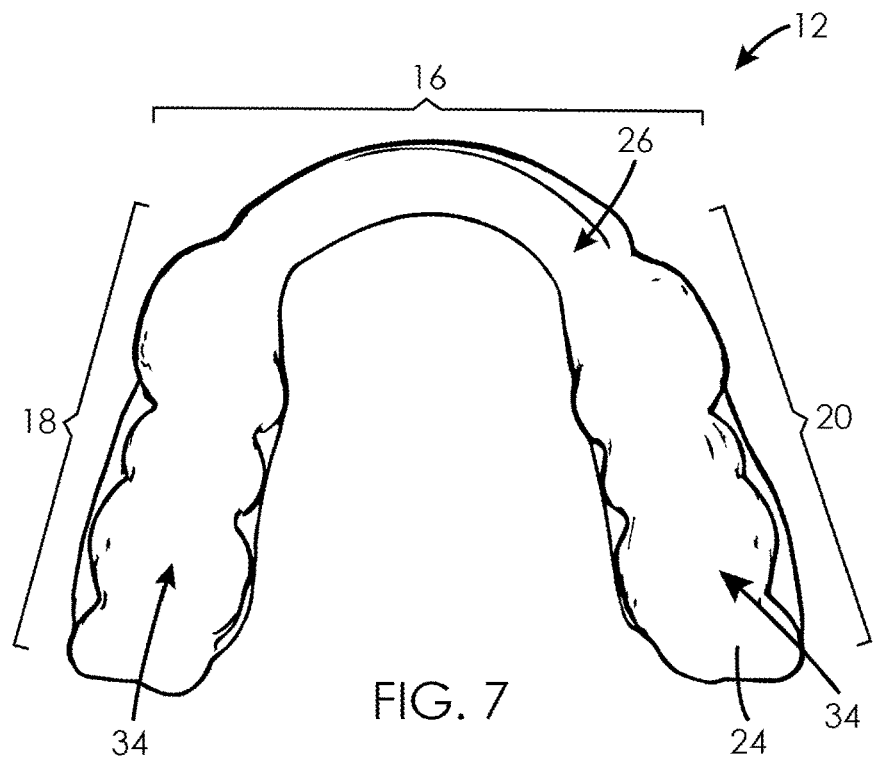
FIG. 7 is a bottom plan view of the maxillary splint shown in FIG. 6.
Figure 8:
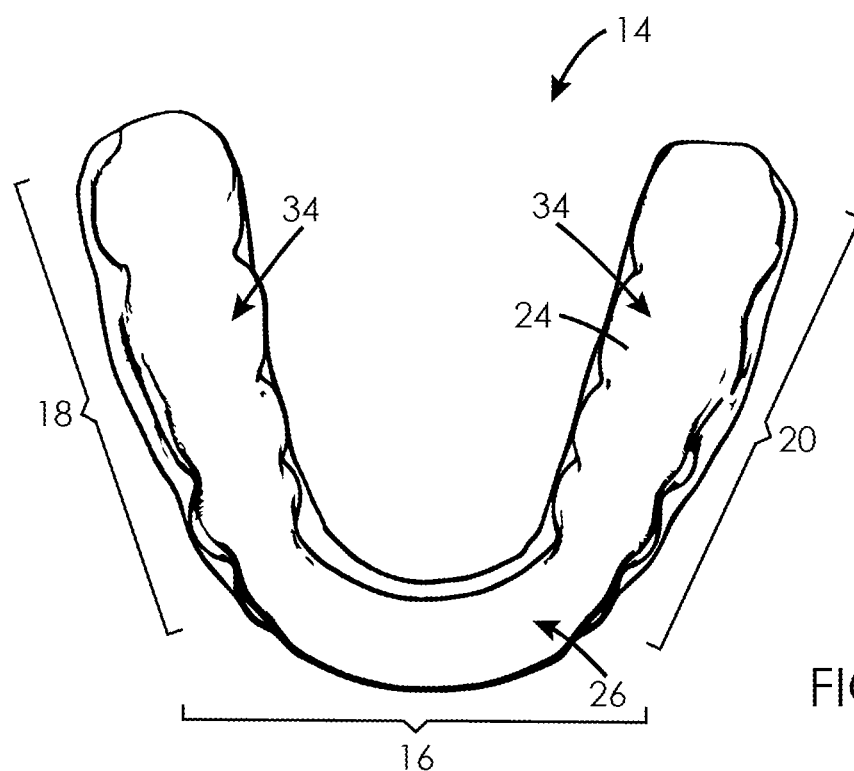
FIG. 8 is a top plan view of the mandibular splint shown in FIG. 1.
Figure 9:
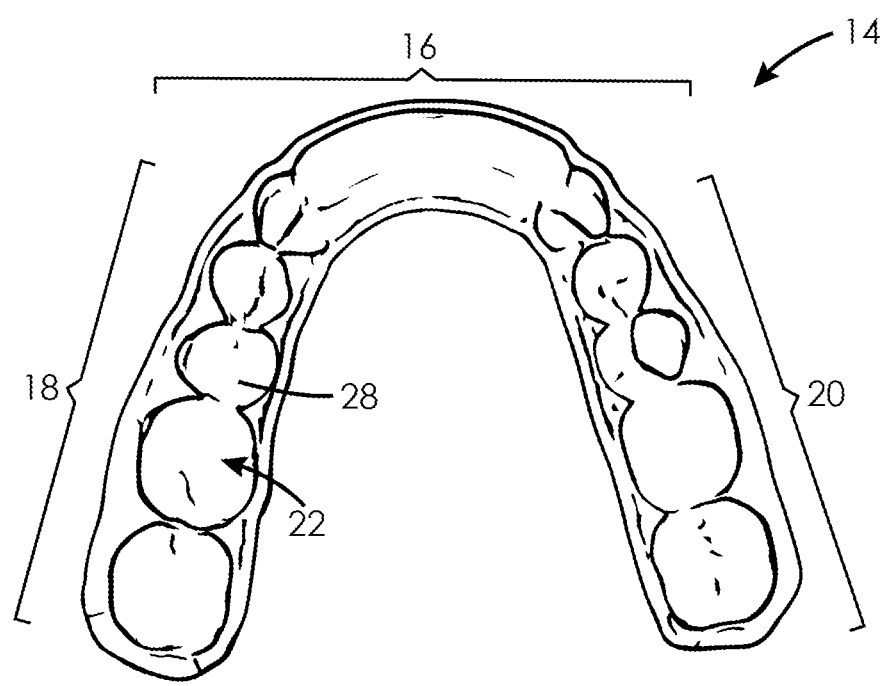
FIG. 9 is a bottom plan view of the mandibular splint shown in FIG. 8.

The splints 12, 14 are operable in a contact (or occlusion or clenched) configuration, as illustrated in FIGS. 2 to 5, wherein the contact surfaces 26 of the maxillary and mandibular splints 12, 14 are abutted one against the other along a plane P (see FIG. 4). The plane P corresponds to the contact plane between the contact surfaces 26 of the maxillary and mandibular splints 12, 14. In the embodiment shown, the contact surfaces 26 are planar surfaces, i.e. the outer wall surfaces 32 at the contact surfaces 26 are substantially flat along the contact plane P. In the contact (or occlusion) configuration, the corresponding posterior sections of the splints 12, 14 are spaced apart, in order to avoid contact therebetween. More particularly, the occlusal faces 34 of the splints 12, 14 are spaced-apart from one another. In an embodiment, they are spaced-apart by at least 0.8 mm.

More particularly, in the embodiment illustrated in the figures, at least one of the posterior sections 18, 20 of the mandibular splint 14 is generally recessed in relation to the contact plane P, as better illustrated in FIG. 4, in order to space apart corresponding posteriors sections 18, 20 of the splints 12, 14 from one another. More particularly, as shown in FIG. 4, in an embodiment, the occlusal faces 34 of the posteriors sections 18, 20 of the mandibular splint 14 are recessed in relation to the contact plane P, i.e. they extend below the contact plane P. The contact surfaces 26 thus provide a support between the splints 12, 14 when they are contacted together, in order to separate the posterior sections 18, 20 of the splints 12, 14 from one another.

In an alternative embodiment (not shown), the occlusal faces 34 of the posteriors sections 18, 20 of the maxillary splint 12 are recessed in relation to the contact plane P. In another alternative embodiment (not shown), the occlusal faces 34 of the posteriors sections 18, 20 of the maxillary splint 12 and the mandibular splint 14 are recessed in relation to the contact plane P.

As can be seen in FIGS. 1, 2, 3, 6 and 9, the inner wall surface 28 of each splint 12, 14 substantially conforms to the shape of the teeth of the corresponding dental arch. The shape of the inner wall surface 28 can be designed by scanning a patient's mouth specifically and designing the inner wall surface 28 to conform to the particular shape of the patient's teeth. In the posterior sections 18, 20 of the splints 12, 14, the outer portion 24 can also substantially conform to and reproduce the shape of the engaged teeth.

Advantageously, when the splints 12, 14 are worn and the dental arches of the wearer are closed together (i.e. when the splints 12, 14 are in the contact configuration), the wearer's bite is limited by the abutting contact surfaces 26 of the anterior sections 16, so as to prevent contact between corresponding posterior teeth including, optionally, the second premolars of the wearer's mouth. Preventing contact between the posterior teeth protects the temporomandibular joint, i.e. the hinge articulation, between the upper and lower jaws, i.e. the maxillary and mandibular jaws. As mentioned above, depending on the size of the mouth, the second premolars are covered by either the anterior section 16 or the posterior sections 18, 20 of the splints 12, 14.

In addition, the planar configuration of the contact surfaces 26 of the anterior sections 16 allow for lateral movement along the contact plane P of the maxillary dental arch in relation to the mandibular dental arch of the wearer's mouth, all the while protecting the articulation between the maxillary and mandibular jaws.

It is to be understood, that the contact surfaces 26 may extend along any suitable location of the splints 12, 14, so as to provide an abutment between the lower and upper dental arches of the wearer's mouth while spacing apart at least the most posterior tooth or teeth between the upper and lower dental arches, in order to protect the articulation of the jaws.

For example, according to varying embodiments, the contact surface 26 of each splint 12, 14 may extend:
   in alignment with the incisive and canine teeth only;
   in alignment with the first and second premolar teeth only;
   in alignment with the canine teeth and first and second premolar teeth only; or
   in alignment with the first and second premolar teeth, as well as with the first molar or a portion thereof.

The anterior section 16 is defined accordingly so as to at least encompass the contact surface(s) 26. It is to be understood also, that the anterior section 16 may comprise two or more contact surfaces 26 for abutting the splints 12, 14 against each other. Indeed, in accordance with some of the above-mentioned examples, abutting contact surfaces 26 may extend toward the sides of the splint 12, 14 (i.e. toward the "ends" of the anterior section 16, close to a junction with the posterior sections 18, 20), which may be suitable for cases where the wearer of the splints 12, 14 has fragile, crooked or absent front teeth, all the while spacing apart at least the most posterior teeth of the bottom dental arch from the corresponding most posterior teeth of the upper dental arch, in order to protect the articulation of the jaws. Other configurations of the contact surface 26 may be suitable depending on the particular state of the teeth of the wearer, as will be readily understood by the person skilled in the art.

In the embodiment shown in the figures, the contact surfaces 26 are planar in order to allow lateral movement along the contact plane P of the maxillary dental arch in relation to the mandibular dental arch of the wearer's mouth. It is to be understood also, that according to alternative embodiments, the abutting contact surfaces 26, may have any shape (for example they may have a relief instead of being planar) which is suitable to allow abutting the anterior portions together while preventing contact between corresponding sets of posterior teeth and, optionally, the second premolars. The abutting contact surfaces 26 of the maxillary and mandibular splints 12, 14 extend substantially parallel to one another in the contact (or clenched) configuration.

In an embodiment, the splints 12, 14 are disconnected from one another when worn, i.e. there is no mechanical connection between the maxillary and mandibular splints 12, 14.

There is also provided a method of making a set of occlusal splints 10 for a mouth. In an embodiment, the method comprises: obtaining models of the maxillary and mandibular dental arches of the mouth. The models can either be a numerical model (or scan model) or a physical 3D model, such as and without being limitative a plaster model. The numerical models can be obtained directly in the patient's mouth. For instance and without being limitative, a scan can be carried out with intraoral camera(s) or a table scanner. They can also be obtained by scanning a physical 3D model. The models are then configured in a centric occlusion configuration wherein the anterior teeth are in contact. To configure the models in the centric occlusion configuration, a model of the centric occlusion can be required. The centric occlusion, also referred to as "bite", consists of the occlusion of opposing teeth when the mandible is in centric relation, i.e. the first tooth contact. Physical models of the centric occlusion are well-known. A numerical model of the centric occlusion can be obtained by scanning the physical mandibular and maxillary models when configured in a centric occlusion configuration. It can also be obtained directly in the patient's mouth by asking the latter to configure its jaws in the centric occlusion configuration and to scan the mouth with an intraoral camera. If the models obtained are numerical models, the models are combined with a suitable software to obtain a 3D global model. This 3D global model represents the patient's jaws in a virtual articulator. The virtual articulator can be used to represent the jaws in the closed and open configurations.

Using the models of the maxillary dental arch and a mandibular dental arch in the contact configuration, the maxillary splint 12 and the mandibular splint 14 are conceived. The anterior and posterior sections 16, 18, 20 are determined. Then, the inner wall surfaces 32 of the splints 12, 14 are designed. In an embodiment, they conform to the shape of teeth aligned therewith. Then, the outer wall surfaces 34 are designed including the contact surfaces 26 of the splints 12, 14. In an embodiment, the contact surfaces 26 are planar and extend substantially parallel to one another in the contact configuration (or occlusion configuration). When designing the outer wall surfaces 34 of the splints 12, 14 in the posterior sections 18, 20, the occlusal faces 34 of the posterior sections 18, 20 are designed to be spaced-apart from one another. In an embodiment, a contact plane P is determined based on the contact surfaces 34 in the anterior sections 16 and at least one of the occlusal faces 34 of the posterior sections 18, 20 is designed to be recessed from the contact plane P. As mentioned above, either the occlusal faces 34 of the maxillary splint 12 or the mandibular splint 14 can be recessed from the contact plane P. In an alternative embodiment, the occlusal faces 34 of both the maxillary splint 12 and the mandibular splint 14 are recessed from the contact plane P.

It is appreciated that the order of the steps for conceiving the splints 12, 14 can differ from the embodiments described above. Additional steps can be performed while one or several steps can be omitted.

Numerous other modifications can be made to the above-described set of occlusal splints 10, without departing from the scope of the present invention. The above-described embodiments are considered in all respect only as illustrative and not restrictive, and the present application is intended to cover any adaptations or variations thereof, as apparent to a person skilled in the art. Of course, numerous other modifications can be made to the above-described embodiments without departing from the scope of the invention, as apparent to a person skilled in the art.

The invention claimed is:

1. A set of occlusal splints comprising:
   a maxillary splint adapted to fit a maxillary dental arch of a mouth; and
   a mandibular splint adapted to fit a mandibular dental arch of the mouth, each one of the maxillary splint and the mandibular splint having an anterior section and two posterior sections extending from opposite ends of the anterior section, and each one of the maxillary splint and the mandibular splint having a body with an inner portion shaped and configured to encase teeth of the corresponding dental arch and an opposed outer portion, the outer portion having a planar contact surface at the anterior section and occlusal faces at the posterior sections, and the maxillary and mandibular splints being operable in a contact configuration, wherein the planar contact surfaces of the maxillary and mandibular splints are abutted one against the other along a contact plane, at least one of the occlusal faces of the posterior sections of the maxillary splint extending above the contact plane and the occlusal faces of the mandibular splint extending below the contact plane, in order to space apart matching occlusal faces of the posterior sections of the maxillary and mandibular splints from one another when the maxillary and mandibular splints are joined in the contact configuration.

2. The set of occlusal splints as claimed in claim 1, wherein at least the mandibular splint comprises recessed posterior sections with the occlusal faces extending below the contact plane.

3. The set of occlusal splints as claimed in claim 1, wherein the body of each one of the maxillary splint and the mandibular splint comprises an inner wall surface substantially conforming to the shape of the teeth of the corresponding dental arch.

4. The set of occlusal splints as claimed in claim 1, wherein the anterior section of each one of the maxillary splint and the mandibular splint covers anterior teeth and at least the first premolar of the corresponding arch when engaged therewith.

5. The set of occlusal splints as claimed in claim 1, wherein the bodies of the maxillary splint and the mandibular splint comprise an outer wall surface and, in the posterior sections, the outer wall surface reproducing a shape of the teeth covered by the corresponding one of the maxillary splint and the mandibular splint.

6. The set of occlusal splints as claimed in claim 1, wherein the planar contact surfaces of the maxillary splint and the mandibular splint extend substantially parallel to one another.

7. The set of occlusal splints as claimed in claim 1, wherein the maxillary splint and the mandibular splint are free of mechanical connector extending therebetween when worn.

8. The set of occlusal splints as claimed in claim 1, wherein the maxillary splint and the mandibular splint are disconnected from one another when worn.

9. A set of occlusal splints, comprising:
a maxillary splint engageable over a maxillary dental arch of a mouth; and
a mandibular splint engageable over a mandibular dental arch of the mouth, each one of the maxillary splint and the mandibular splint having an anterior section and two posterior sections extending from opposite ends of the anterior section, and each one of the maxillary splint and the mandibular splint having an inner portion shaped and configured to encase teeth of the corresponding one of the dental arches and an opposed outer portion, the outer portion having a contact surface at the anterior section and occlusal faces at the posterior sections, and the maxillary splint and the mandibular splint being operable in a contact configuration, wherein the contact surfaces of the maxillary and mandibular splints are abutted one against the other, and wherein corresponding ones of the occlusal faces at the posterior sections are spaced apart, in order to protect the articulation between upper and lower jaws of the mouth.

10. The set of occlusal splints as claimed in claim 9, wherein the contact surfaces are substantially planar.

11. The set of occlusal splints as claimed in claim 9, wherein each one of the maxillary splint and the mandibular splint comprises an inner wall surface substantially conforming to the shape of the teeth of the corresponding dental arch.

12. The set of occlusal splints as claimed in claim 9, wherein the anterior section of each one of the maxillary splint and the mandibular splint covers anterior teeth and at least the first premolar of the corresponding arch when engaged therewith.

13. The set of occlusal splints as claimed in claim 9, wherein the maxillary splint and the mandibular splint comprise an outer wall surface and, in the posterior sections, the outer wall surface reproducing a shape of the teeth covered by the corresponding one of the maxillary splint and the mandibular splint.

14. The set of occlusal splints as claimed in claim 9, wherein the contact surfaces of the maxillary splint and the mandibular splint extend substantially parallel to one another.

15. The set of occlusal splints as claimed in claim 9, wherein the maxillary splint and the mandibular splint are disconnected from one another when worn.

16. The set of occlusal splints as claimed in claim 9, further comprising a contact plane defined between the contact surfaces in the contact configuration, wherein at least the occlusal faces in the posterior sections of the mandibular splint extend below the contact plane.

17. A set of occlusal splints, comprising:
a maxillary splint engageable over a maxillary superior dental arch of a mouth; and
a mandibular splint engageable over a mandibular dental arch of the mouth, each one of the maxillary splint and the mandibular splint being substantially U-shaped with an anterior section and two posterior sections extending from opposite ends of the anterior section, and each one of the maxillary splint and the mandibular splint having an inner wall surface defining a cavity shaped and configured to encase teeth of the corresponding one of the dental arches and an opposed outer wall surface, the outer wall surface having a contact surface at the anterior section and an occlusal face at the posterior section, and the maxillary and mandibular splints being operable in a contact configuration, wherein the contact surfaces of the maxillary and mandibular splints are abutted one against the other, and wherein the occlusal face of the posterior sections are spaced apart from one another.

18. The set of occlusal splints as claimed in claim 17, wherein the contact surfaces are substantially flat.

19. The set of occlusal splints as claimed in claim 17, wherein each one of the maxillary splint and the mandibular splint comprises an inner wall surface substantially conforming to the shape of the teeth of the corresponding dental arch.

20. The set of occlusal splints as claimed in claim 17, wherein the anterior section of each one of the maxillary splint and the mandibular splint covers anterior teeth and at least the first premolar of the corresponding arch when engaged therewith.

21. The set of occlusal splints as claimed in claim 17, wherein, in the posterior sections, the outer wall surface of the maxillary splint and the mandibular splint reproduces a shape of the teeth covered by the corresponding one of the maxillary splint and the mandibular splint.

22. The set of occlusal splints as claimed in claim 17, wherein the contact surfaces of the maxillary splint and the mandibular splint extend substantially parallel to one another.

23. The set of occlusal splints as claimed in claim 17, wherein the maxillary splint and the mandibular splint are free of mechanical connector extending therebetween when worn.

24. The set of occlusal splints as claimed in claim 17, further comprising a contact plane defined between the contact surfaces in the contact configuration, wherein at least the occlusal faces in the posterior sections of the mandibular splint extend below the contact plane.

* * * * *